US010201266B2

United States Patent
Wang et al.

(10) Patent No.: US 10,201,266 B2
(45) Date of Patent: Feb. 12, 2019

(54) SINGLE IMAGE SENSOR CONTROL FOR CAPTURING MIXED MODE IMAGES

(71) Applicant: CAPSOVISION, INC., Saratoga, CA (US)

(72) Inventors: Kang-Huai Wang, Saratoga, CA (US); Mark Hadley, Newark, CA (US); Chung-Ta Lee, Sunnyvale, CA (US); Chang-Wei Lin, Mountain View, CA (US)

( * ) Notice: Subject to any disclaimer, the term of this patent is extended or adjusted under 35 U.S.C. 154(b) by 104 days.

(21) Appl. No.: 15/613,205

(22) Filed: Jun. 3, 2017

(65) Prior Publication Data

US 2017/0265730 A1 Sep. 21, 2017

Related U.S. Application Data

(63) Continuation-in-part of application No. 15/333,071, filed on Oct. 24, 2016, which is a continuation-in-part
(Continued)

(51) Int. Cl.
*A61B 1/04* (2006.01)
*A61B 1/06* (2006.01)
(Continued)

(52) U.S. Cl.
CPC ............... *A61B 1/041* (2013.01); *A61B 1/06* (2013.01); *G01B 11/2513* (2013.01); *H04N 5/2256* (2013.01); *H04N 5/23245* (2013.01); *H04N 5/3532* (2013.01); *H04N 5/35581* (2013.01); *H04N 9/045* (2013.01); *H04N 13/254* (2018.05); *H04N 13/296* (2018.05);
(Continued)

(58) Field of Classification Search
CPC .. A61B 1/06; H04N 13/0253; H04N 13/0296; H04N 2201/0079
USPC .......................................................... 348/46
See application file for complete search history.

(56) References Cited

U.S. PATENT DOCUMENTS

| 7,983,458 B2 | 7/2011 | Wang |
| 8,369,458 B2 | 2/2013 | Wong et al. |
| 2009/0259102 A1* | 10/2009 | Koninckx .......... A61B 1/00181 600/111 |

OTHER PUBLICATIONS

Geng, "Structured-light 3D surface imaging: a tutorial", in Advances in Optics and Photonics, vol. 3, Issue 2, pp. 128-160, Mar. 31, 2011.
(Continued)

*Primary Examiner* — Hee-Yong Kim
(74) *Attorney, Agent, or Firm* — Blairtech Solution LLC

(57) ABSTRACT

A method and apparatus for capturing an image sequence using a capsule camera are disclosed. According to the present invention, a first energy-based frame time for the special images is determined based on first light energy perceived by the image sensor and a second energy-based frame time for the regular images is determined based on second light energy perceived by the image sensor. The capsule camera captures the image sequence comprising one or more sets of mixed-type images by configuring the capsule camera to cause a mixed-frame distance between the first energy-based frame time for one special image in a target set of mixed-type images and the second energy-based frame time for one regular image in the target set of mixed-type images smaller than an average frame period.

20 Claims, 5 Drawing Sheets

Related U.S. Application Data of application No. 14/884,788, filed on Oct. 16, 2015, now Pat. No. 9,936,151.

(60) Provisional application No. 62/268,975, filed on Dec. 17, 2015.

(51) Int. Cl.

| | |
|---|---|
| *H04N 13/254* | (2018.01) |
| *H04N 13/296* | (2018.01) |
| *G01B 11/25* | (2006.01) |
| *H04N 5/225* | (2006.01) |
| *H04N 5/232* | (2006.01) |
| *H04N 5/353* | (2011.01) |
| *H04N 5/355* | (2011.01) |
| *H04N 9/04* | (2006.01) |

(52) U.S. Cl.
CPC ............... *H04N 2005/2255* (2013.01); *H04N 2201/0079* (2013.01)

(56) References Cited

OTHER PUBLICATIONS

DePiero et al., Advances in Computers, vol. 43, Jan. 1, 1996, pp. 243-278.

* cited by examiner

SINGLE IMAGE SENSOR CONTROL FOR CAPTURING MIXED MODE IMAGES

CROSS REFERENCE TO RELATED APPLICATIONS

The present invention is a Continuation-in-Part Application of and claims priority to U.S. Non-Provisional patent application Ser. No. 14/884,788, filed on Oct. 16, 2015. The present invention is also a Continuation-in-Part Application of and claims priority to U.S. Non-Provisional patent application Ser. No. 15/333,071, filed on Oct. 24, 2016, which is a Continuation-in-Part Application of and claims priority to U.S. Non-Provisional patent application Ser. No. 14/884, 788, filed on Oct. 16, 2015. The U.S. Non-Provisional patent application Ser. No. 15/333,071 also claims priority to U.S. Provisional Application, Ser. No. 62/268,975, filed on Dec. 17, 2015. The U.S. Non-Provisional Patent Applications and U.S. Provisional Patent Application are hereby incorporated by reference in their entireties.

FIELD OF THE INVENTION

The present invention relates to a single image sensor and its control capable of capturing images in different modes efficiently and optimally.

BACKGROUND AND RELATED ART

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools.

Capsule endoscope is an alternative in vivo endoscope developed in recent years. For capsule endoscope, a camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An autonomous capsule camera system with on-board data storage was disclosed in the U.S. Pat. No. 7,983,458, entitled "In Vivo Autonomous Camera with On-Board Data Storage or Digital Wireless Transmission in Regulatory Approved Band," granted on Jul. 19, 2011. The capsule camera with on-board storage archives the captured images in on-board non-volatile memory. The capsule camera is retrieved upon its exiting from the human body. The images stored in the non-volatile memory of the retrieved capsule camera are then accessed through an output port on in the capsule camera.

While the two-dimensional images captured by the endoscopes have been shown useful for diagnosis, it is desirable to be able to capture gastrointestinal (GI) tract images with depth information (i.e., three-dimensional (3D) images) to improve the accuracy of diagnosis or to ease the diagnosis process. In the field of 3D imaging, 3D images may be captured using a regular camera for the texture information in the scene and a separate depth camera (e.g. Time of Flight camera) for the depth information of the scene in the field of view. The 3D images may also be captured using multiple cameras, where multiple cameras are often used in a planar configuration to capture a scene from different view angles. Then, point correspondence is established among multiple views for 3D triangulation. Nevertheless, these multi-camera systems may not be easily adapted to the GI tract environment, where the space is very limited. In the past twenty years, a structured light technology has been developed to derive the depth or shape of objects in the scene using a single camera. In the structured light system, a light source, often a projector is used to project known geometric pattern(s) onto objects in the scene. A regular camera can be used to capture images with and without the projected patterns. The images captured with the structured light can be used to derive the shapes associated with the objects in the scene. The depth or shape information is then used with regular images, which are captured with non-structured floodlit light, to create 3D textured model of the objects. The structured light technology has been well known in the field. For example, in "*Structured-light 3D surface imaging: a tutorial*" (Geng, in *Advances in Optics and Photonics*, Vol. 3, Issue 2, pp. 128-160, Mar. 31, 2011), structured light technology using various structured light patterns are described and the corresponding performances are compared. In another example, various design, calibration and implement issues are described in "3-D Computer Vision Using Structured Light: Design, Calibration and Implementation Issues" (DePiero et al., *Advances in Computers*, Volume 43, Jan. 1, 1996, pages 243-278). Accordingly, the details of the structured light technology are not repeated here.

The structured light technology may be more suitable for 3D imaging of the GI tract than other technologies. However, there are still issues with the intended application for GI tract. For example, most of the structured light applications are intended for stationary object. Therefore, there is no object movement between the captured structured-light image and the regular image. Nevertheless, in the capsule camera application for GI tract imaging, both the capsule camera and the GI parts (e.g. small intestines and colons) may be moving. Therefore, there will be relative movement between the structured-light image and the regular image if they are captured consecutively, in particular under the circumstance of low frame rate. Furthermore, the capsule camera application is a very power-sensitive environment. The use of structured light will consume system power in addition to capturing the regular images. Besides, if one structured light image is taken associated with each regular image, the useful frame rate will be dropped to about half. If the same frame rate of regular images is maintained, the system would have to capture images at twice the regular frame rate and consume roughly twice the power in image capture.

Accordingly, U.S. patent application Ser. No. 14/884,788 discloses technologies for structured light application in the GI tract that can overcome the power issue and capture time difference issue as mentioned above. For example, techniques have been disclosed to allow structured light image captured with shortened frame time and lower power by using an analog-to-digital converter with lower dynamic range. In U.S. patent application Ser. No. 14/884,788, the aspect of controlling the capture of two structured light images for a regular image has been disclosed to further improve the accuracy of depth information associated with a corresponding regular image.

In the application of structured light image, mixed-type images (i.e., structured light image and regular light image) are captured. The structured light image is used to derive the depth information for an associated regular light image. Usually, the depth information does not require having the same spatial resolution requirement or the same bit depth as the corresponding texture information in the regular light image.

There are also other situations of capturing mixed-type images. For example, in U.S. Pat. No. 7,940,973 issued on May 10, 2011, a capsule camera with capture control is disclosed, where the sensor is configured to support the Monitor mode and the Capture mode, where the Monitor mode is operated in low power without the need to store or transmit the generated image. On the other hand, the Capture mode captures images for storage or transmission that will be viewed for diagnosis purposes. Therefore, the images in the Monitor mode can use lower quality and the Capture mode will use higher quality to preserve features of diagnostic interest. In this application, the camera switches to the Capture mode whenever motion or activities are detected. It is desirable to be able to switch from the Monitor mode to the Capture mode as soon as possible when motion or activities are detected. The quick switch may avoid the possibility of missing important diagnostic information during image capture.

BRIEF SUMMARY OF THE INVENTION

A method and apparatus for capturing an image sequence using a capsule camera when the capsule camera travels through a human gastrointestinal tract after the capsule camera is swallowed by a patient are disclosed. The capsule camera comprises an image sensor and is capable of capturing at least two mixed-type images corresponding to special images and regular images. According to the present invention, a first energy-based frame time for the special images is determined based on first light energy perceived by the image sensor and a second energy-based frame time for the regular images is determined based on second light energy perceived by the image sensor. The capsule camera captures the image sequence comprising one or more sets of mixed-type images by configuring the capsule camera to cause a mixed-frame distance between the first energy-based frame time for one special image in a target set of mixed-type images and the second energy-based frame time for one regular image in the target set of mixed-type images smaller than an average frame period. Each set of mixed-type images comprises at least one special image and one regular image. The image sequence captured is then provided for further processing or outputted. The special images are used to control capturing the regular images or used to derive or provide associated information for the regular images. Furthermore, the image sequence is captured at an overall average frame rate substantially lower than a capable frame rate of the capsule camera, where the overall average frame rate is calculated as a sum of individual frame rates of mixed-type images. For example, if the mixed-type images consist of first type images and second type images. The average frame rate of the first type images is $f_1$ and the average frame rate of the second type images is $f_2$, the overall average frame rate $f_0$ is equal to $(f_1+f_2)$.

The first light energy perceived by the image sensor is determined by accumulating first illumination power from a light source over a first integration period of the image sensor for the special images and the second light energy perceived by the image sensor is determined by accumulating second illumination power from the light source over a second integration period of the image sensor for the regular images. The first energy-based frame time is determined at a first time instance when the first light energy exceeds a first energy threshold for a target special image and the second energy-based frame time is determined at a second time instance when the second light energy exceeds a second energy threshold for a target regular image. In one embodiment, the first energy threshold is set to a half of maximum first light energy and the second energy threshold is set to a half of total accumulated second light energy.

In one embodiment, the mixed-frame time distance is smaller than a half of the overall average frame period $T_0$, where the overall average frame period is calculated as the inverse of the overall average frame rate. The special images may be captured with lower quality. The lower quality may correspond to lower image dynamic range, lower spatial resolution, smaller image size, or a combination thereof.

In one application, the special images correspond to structured-light images (SLIs) used to derive depth information for associated regular images. Each set of mixed-type images consists of one structured-light image (SLI) and one regular image. The structured-light image (SLI) is captured prior to the regular image in one embodiment and the structured-light image (SLI) is captured after the regular image in another embodiment. Each set of mixed-type images may also consist of one structured-light image (SLI) and two regular sub-images according to another embodiment, where the structured-light image is captured between the two regular sub-images and the mixed-frame time distance is derived based on two mixed-frame time distances associated with the structured-light image and the two regular sub-images respectively. Furthermore, the two regular sub-images can be combined to form one regular image. Details of capturing two regular sub-images and combining them into one regular image have been disclosed in U.S. Non-Provisional patent application Ser. No. 14/884,788, filed on Oct. 16, 2015.

In another application, the special images correspond to monitor-mode images used to control capturing the regular images. Each set of mixed-type images may consist of one monitor-mode image and one or more regular images. In one embodiment, an activity metric is determined between one monitor-mode image and one previously captured image, and when the activity metric exceeds a threshold, one or more regular images are captured to form one set of mixed-types of images along with said one monitor-mode image. On the other hand, when the activity metric does not exceed the threshold, a next monitor-mode image is captured.

In yet another application, the special images correspond to narrow-band images and the regular images correspond to wide-band images. Each set of mixed-type images consists of one wide-band image and narrow-band images.

BRIEF DESCRIPTION OF THE DRAWINGS

FIG. 11 illustrates an embodiment of the present invention, where two regular sub-images are captured with an SLI captured in between.

FIG. 12 illustrates an embodiment of the present invention, where two special images (narrow-band images) are captured with a regular image (wideband image) captured in between.

DETAILED DESCRIPTION OF THE INVENTION

Figure 1:
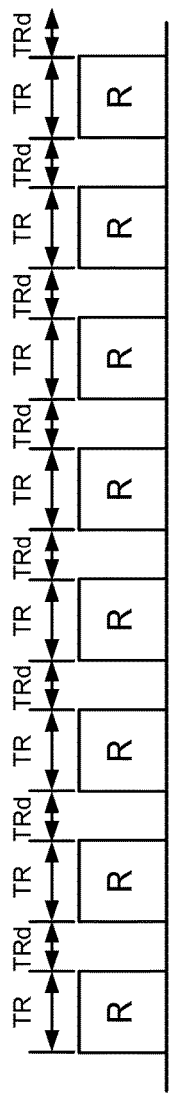
FIG. 1 illustrates an example of image sequence capture using an image sensor, where the image sensor is operated at a typical frame rate (e.g. 30 frames per second) for video data.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention. References throughout this specification to "one embodiment," "an embodiment," or similar language mean that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, components, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

Endoscopes are normally inserted into the human body through a natural opening such as the mouth or anus. Therefore, endoscopes are preferred to be small sizes so as to be minimally invasive. To derive or capture the depth or shape information while capturing live images or videos of the GI tract with endoscopes, it is crucial to maintain the small-size form factor. Besides, with the small size and the capability to capture depth information along with corresponding images or video, such camera also finds its applications in other applications requiring compact size, such as a wearable devices.

One technique that may capture depth information is to use a color filter placed on top of selected sensor pixels with the passband reasonably narrow and capture the color information and depth information simultaneously. The environment light sources with spectrum in the filter passband will cause negligible amount of energy projected onto the sensor. For the case of RGB pixels, a fourth type of pixels may be added to capture light with the spectrum in the passband of the filter placed on top of these pixels. Then, the structured light that has the spectrum substantially in the passband can be projected onto the scene. However, this approach will reduce the spatial resolution of the images or video captured using such image sensor.

Another technique is to obtain the depth information as well as 3D topology by projecting structured light patterns that are visible in the RGB sensors. However the real time image and/or video will be confounded by the structured light superimposed on it. This invention describes methods to use a single camera to achieve depth information by using the structured light approach while taking images or real time video using the camera.

In another embodiment, the structure light pattern is projected with much higher intensity than the regular light intensity on the sensor surface such that the structure light pattern can still be discerned.

As mentioned before, a conventional structured light approach with a single camera would incur several drawbacks. For example, the camera with a frame rate of 5 frames per second may be used. A conventional approach would capture an image sequence with interleaved images corresponding to images with and without the structured light. One issue is that the depth information is ⅕ second away from corresponding images to be viewed. If there is any movement in the scene, the depth information may not accurately represent the 3D topology of the corresponding images at ⅕ second away. In addition, the effective frame rate for the video to be viewed is dropped to 2.5 frames per second in this example.

FIG. 1 illustrates an example of image sequence capture using an image sensor. The image sensor is operated at a typical frame rate (e.g. 30 frames per second) for video data. In FIG. 1, each regular image (R) has an active period TR and a delay period TRd. The active period TR may comprise times required for reset, exposure, light integration, and readout. The active period may further comprise image processing time. Since the sensor may not have to operate at a full frame rate limit associated with the image sensor, a delay period may exist between two active frame periods. The delay period may be relatively short compared to the active period. The delay period may also be zero. Furthermore, the delay period can be reduced by operating the sensor at a slower pixel clock.

Figure 2:
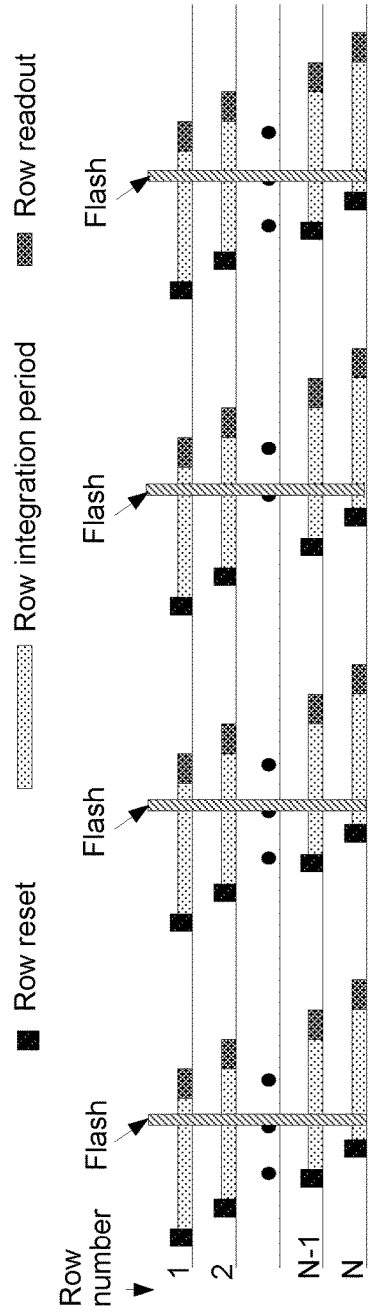
FIG. 2 illustrates an example of detailed frame timing for a sensor operated in a sequential row reading mode.

FIG. 2 illustrates an example of detailed frame timing for sequential row reading sensor mode. According to the conventional sensor capture method, the rows are reset, charge-integrated and read out sequentially. The periods for row reset, integration and readout are shown by different fill-patterns. The frame is read out row by row from the beginning of first row readout to the end of the last row readout. The drawings are intended to indicate the operations associated with the sequential row reading mode and the periods may not be drawn in scale. The illumination period is also indicated in the drawing by "Flash". In FIG. 2, some delay between frames is also indicated, where the first row start for a next frame occurs at a time after the last readout of the current frame. In practice, the first row start for a next frame occurs can occur immediately after the last readout of the current frame. Furthermore, the first row start for a next frame occurs can even start before the last readout of the current frame.

For a capsule camera, the images for the gastrointestinal (GI) tract are normally a few frames per second since the capsule moves slowly in the GI tract. Also, in vivo capsule camera is typically operated on small button batteries inside the capsule device and the power is a precious resource for the capsule device. For capsule camera with on-board storage, the storage space typically is limited. Accordingly, even though the capsule camera is capable of capturing images at a much higher frame rate (e.g. 30 frames per second, fps), the actual capture rate is kept relatively low, such as 2 to 5 frames per second in order to conserve power and/or on-board storage space.

Figure 3:
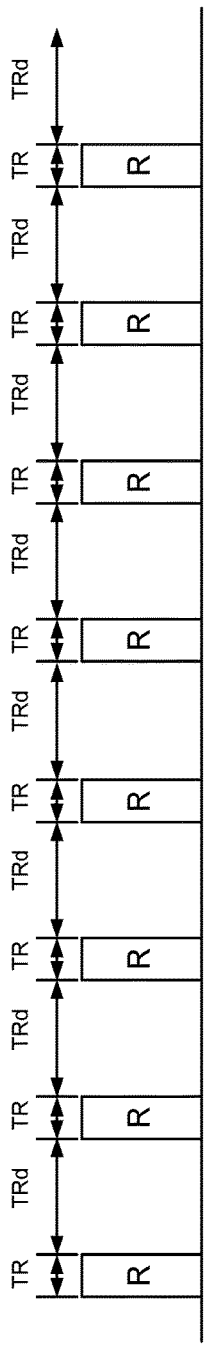
FIG. 3 illustrates an example of capturing an image sequence at a frame rate (e.g. 2 to 5 fps) noticeably or substantially lower than the capable frame rate (e.g. 30 fps) of the sensor.

FIG. 3 illustrates an example of capturing an image sequence at a frame rate (e.g. 2 to 5 fps) noticeably or substantially lower than the capable frame rate (e.g. 30 fps) of the sensor. Since the frame rate is much lower than the capable video frame rate, the next frame usually waits for a period of time before the next frame starts. In other words, there is a period of delay after the current frame is captured and the next frame is started. As shown in FIG. 3, the active frame time TR and frame delay time TRd are indicated, where the frame delay (TRd) is much longer than that for the normal video capture in FIG. 1. As mentioned earlier, the delay is a period that can be reduced to substantially zero (i.e., TRd≥0).

For certain imaging applications, there is a need to capture two different types of images using the same camera, where one type of images may have lower quality, such as lower resolution, smaller image size or lower bit depth. For example, in U.S. Pat. No. 7,940,973 issued on May 10, 2011, a capsule camera system with image capture control is disclosed, where the sensor stays in a Monitor mode to capture temporary images using less energy in order to conserve power. The temporary images are intended for evaluating motion in the scene and are not stored in the archival memory nor transmitted to an external receiving unit. When motion is detected in the scene, the sensor is switched to a capture mode or regular mode to capture and to store/transmit regular images in good quality for diagnosis purpose. In U.S. patent application Ser. No. 14/884,788, filed on Oct. 16, 2015, a capsule camera system for capturing mixed structured-light images (SLIs) and regular images is disclosed, where the SLIs are captured by setting the sensor to a lower dynamic range. Accordingly, the SLIs are captured using less bit depth and/or lower resolution. Accordingly, the SLIs have lower image quality corresponding to lower spatial resolution and/or lower dynamic range (i.e., less bit depth) than the regular images. The depth information for regular images is derived from the associated SLIs. Since the structured light image for depth information usually doesn't need to have the same bit depth or the same spatial resolution as the regular images, the SLIs can be captured in lower image quality corresponding to lower spatial resolution and/or less bit depth. In yet another example of two-type image capture, narrow-band imaging may be used along with wideband imaging in endoscope application, where the narrow-band images may be used to better discern the pathology of interest. For example, in PCT Application No. PCT/US13/77899, filed on Dec. 27, 2013, a capsule camera device with multi-spectral light sources is disclosed, where images are captured with at least two selected light spectrum. The image associated with one spectrum (e.g. narrowband) may be treated as the lower-quality mode and the other spectrum (e.g. wideband) may be treated as a regular (or higher quality) mode.

In the case of image capture with a capture mode (i.e., the regular mode) and a monitor mode, when activity or motion is detected in the monitor mode, it is desirable to switch to the capture mode as soon as possible since any delay may cause missing important anomaly in the GI tract. In the case of structured-light imaging, the depth information derived from the SLIs will be used by associated regular images. Since an SLI and an associated regular image are captured at two different time instances, the scenes in the SLI and the associated regular image may be different due to camera movement between the two time instances. Therefore, it is desirable to shorten the time difference between the two time instances so that the depth information derived from the SLI will have a better match with the true depth of the associated regular image. In the case of narrow-band imaging, it is desirable to capture the images in different spectral bands as close in time as possible.

Figure 4:
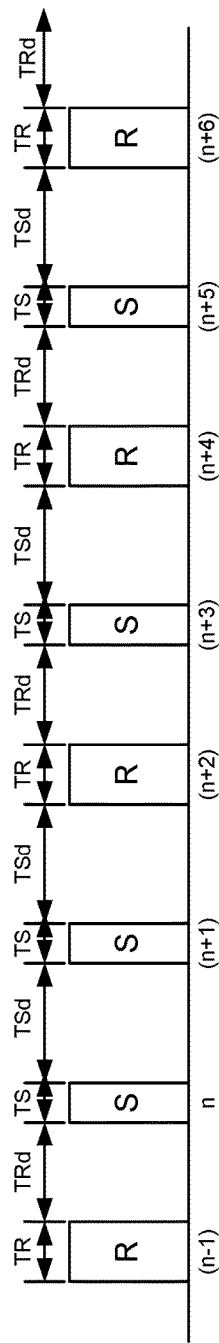
FIG. 4 illustrates an example of capturing mixed types of images according to a conventional approach, where R indicates regular images and S indicates special images (e.g. monitor-mode images).

FIG. 4 illustrates an example of capturing mixed types of images according to a conventional approach, where R indicates regular images and S indicates special images (a monitor-mode image in this example). The special image may correspond to an image in the monitor mode, a SLI, or a narrow-band image. The special image may have the same quality, in terms of spatial resolution, image size, bit depth or a combination, as the regular image. However, often the special image has lower quality in order to conserve energy and/or other resources. In the example of FIG. 4, the special images (e.g. the monitor-mode images) are captured with smaller image size and each special image has a shorter active period (TS) compared to the active period of the regular image (TR). In this example, the frame starts periodically at a frame start time regardless whether it is a regular frame or a special frame. Therefore, the delay time for the special images is slightly longer so that the total frame time (i.e., the active period plus the delay time) is the same for the regular image and the special image (i.e., (TR+TRd)=(TS+TSd)). For image capture control using mixed-type images (i.e., regular images and monitor-mode images), the camera stays in the monitor mode to conserve energy until activities in the scene are detected. When activity or motion is detected, the camera is switched to the regular mode to capture good quality image (e.g. full image quality) when activity or motion is detected. In FIG. 4, frame n is a special image with no activity or motion detected and the next frame (i.e., n+1) stays in the monitor mode. If motion is detected in frame (n+1), the next frame (i.e., n+2) is captured in the regular mode and the camera goes to the monitor mode for the next frame (i.e., n+3). Other operating variations may also be used. For example, instead of a single regular image, multiple regular images can be captured every time when motion is detected.

In order to determine whether to capture the next image in the regular mode, an activity metric can be define based on a current image and a previously captured image. If the activity metric satisfies a condition, movement is declared and the capsule camera enters the capture mode to capture a good-quality image for storing or to transmitting. For example, if the activity metric exceeds a threshold, movement is declared and the capsule camera enters the capture mode. Various activity metrics are disclosed in U.S. Pat. No. 7,940,973.

The intent of "capturing a regular image and an associated special image as close in time as possible" may be understood differently in practice since a "frame time" may be defined differently. For example, a "frame time" may be defined as based on the beginning time to capture an image, the center of active frame period, the time instance of last row readout, etc. These frame times may not necessarily correlate with the contents in a most meaningful way. For example, if an image is captured in a dark environment (e.g. images of the GI tract captured using a capsule camera) and the light energy totally relies on the illumination from the light source (e.g. LEDs) in the capsule device. In this case, the contents are more related to the time period with the LEDs being on. Therefore, the time difference between a regular image and an associated special image are mostly determined by the periods of LEDs being on (assuming the flash period being short and other sensor setting being the same). In order to identify a "frame time" that can be closely related to the time corresponding to the contents of the image being captured, an energy-based frame time is disclosed in the present invention.

Figure 5:
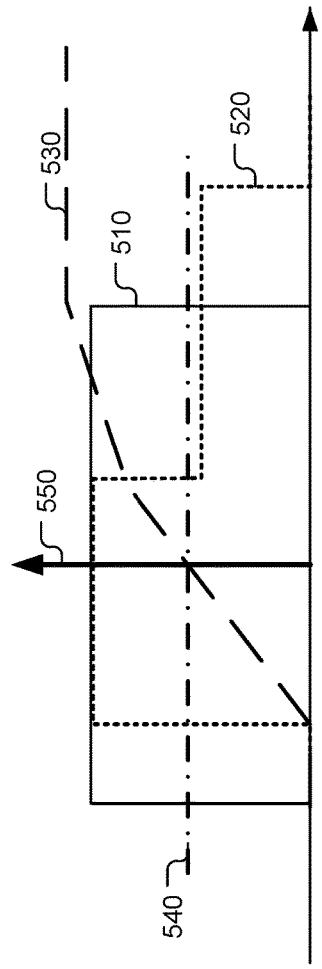
FIG. 5 illustrates an example of timing signals related to image capture, where integration period and illumination power profile are shown.

FIG. 5 illustrates an example of timing signals related to image capture, where integration period 510 and illumination power profile 520 of the light source are shown. As known in the imaging field, the charges integrated by the sensor pixels are proportional to the light energy during the integration period by converting the light energy to electrical energy via a transfer function, which may be non-linear. The illumination energy 530 is indicated, which doesn't further increase after the integration period. The actual light energy for each pixel also depends on the reflectance from an object in the scene. However, the energy-based frame time only cares for the relative energy accumulated. Therefore, the reflectance variations among pixels are ignored during the determination of energy-based frame time. The energy-based frame time is defined as a time instance that the light energy reaches a pre-defined level. For example, the energy level (540) can be equal to 50% of the total light energy and the corresponding energy-based frame time (550) is referred as half-energy frame time in this disclosure. However, other energy level may also be used. In FIG. 5, the profile of the illumination power has two power levels. However, a single power level or more than two power levels may be used as well. While the illumination power stays on beyond the integration period, the illumination often is applied within the integration period. Furthermore, the period of the illumination may be relatively short. In practice, other illumination controls may be applied to the light source to result in other illumination profiles.

Figure 6:
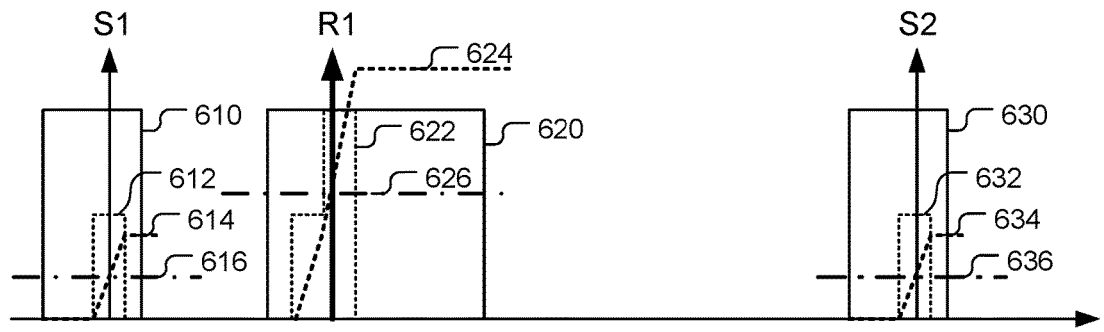
FIG. 6 illustrates an example of signal timings for a special image followed by a regular image, where the integration periods, illumination profiles, illumination energies and half-energy levels are shown for the special images and the regular image respectively.

FIG. 6 illustrates an example of signal timings for a special image followed by a regular image. In FIG. 6, the integration periods (610 and 630), illumination profiles (612 and 632), illumination energies (614 and 634) and half-energy levels (616 and 636) are shown for special images S1 and S2 respectively. The integration period (620), illumination profile (622), illumination energy (624) and half-energy level (626) for regular image R are also indicated. The half-energy frame times are indicated by the upward arrows for respective images S1, R1 and S2. As shown in the example, the special images are captured using a shorter integration period, shorter illumination period. Furthermore, the illumination period is located after the mid-point of the integration period in order to move the energy-based frame time for the special image toward the energy-based frame time of the regular image. On the other hand, the integration period and the illumination period of the regular image are longer than those of the corresponding special images. Furthermore, the illumination starts during an early part of the integration period and two different illumination power levels are used. In addition, the delay period between the special image and the associated regular image is substantially reduced to cause the half-energy frame times of the special image and the associated regular image closer than the average frame period. Since the capsule camera is often operated at a frame rate much lower than the capable frame rate of the sensor, the delay period is often longer than half of the average frame period. In another embodiment, the Tsd (i.e., frame delay) for S1 is made shorter than that as indicated in FIG. 4 so as to shorten the time distance between S1 and R1. Therefore, according to embodiments of the present invention, the half-energy frame times of the special image and the associated regular image can be substantial reduced, such as to less than half of the average frame period.

Figure 7:
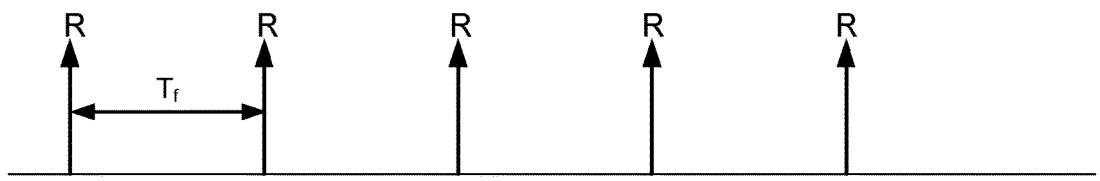
FIG. 7 illustrates an example of the half-energy frame times for a capsule camera that only captures regular images, where the frame period $T_f$ is indicated.
Figure 8:
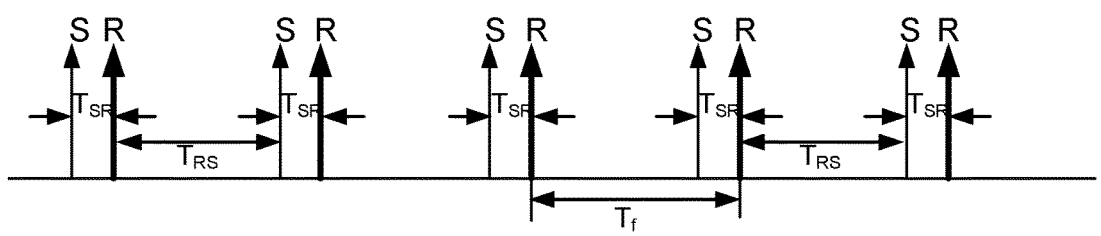
FIG. 8 illustrates an example of a capsule camera that uses image capture control according to an embodiment of the present invention.
Figure 9:
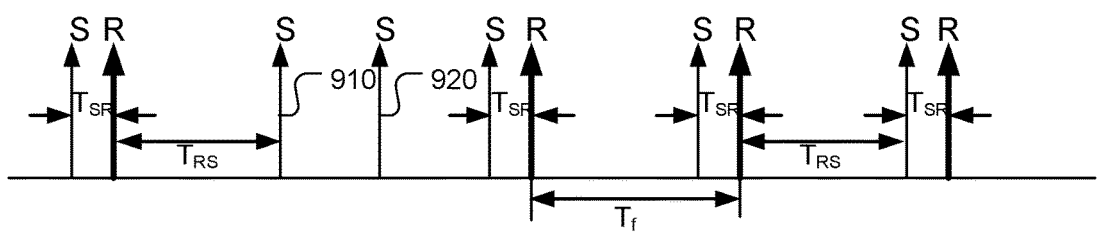
FIG. 9 illustrates another example similar to that in FIG. 8, however, no motion is detected for some special images in the current example.

FIG. 7 illustrates an example of the half-energy frame times for a capsule camera that only captures regular images. The frame period $T_f$ is indicated. FIG. 8 illustrates an example of a capsule camera that uses image capture control according to an embodiment of the present invention. The special image corresponds to monitor-mode image that is used to control whether the next frame should be a regular image or not. If motion is detected, the next frame will be captured in the regular mode, where the energy-based frame time is of the regular image is made to be closer to the energy-based frame time of the associated monitor-mode image by configuring the image sensor. In the example of FIG. 8, motion is detected at every monitor image. Therefore, a regular image is captured after each monitor image. Furthermore, in this example, the total frame rate for the special image and the regular image is twice of the frame rate for regular images along in FIG. 7. Therefore, the system can capture regular image at the same frame rate as a capture system that doesn't use capture control. The half-energy frame times from a special image to a regular image is designated as $T_{SR}$. Similarly, the half-energy frame times from a regular image to a special image is designated as $T_{RS}$. As shown in FIG. 8, $T_{SR}$ is smaller than the average frame period (i.e., ½ $T_f$). FIG. 9 illustrates another example similar to that in FIG. 8. However, in this example, no motion is detected for special image 910. Therefore, another special image 920 is captured to determine whether there is detected motion in the scene. After a regular image is captured, the capsule camera is switched to the monitor mode again. However, as mentioned earlier, it is also possible to capture more than one regular image if activity metric exceeds a threshold or motion is detected. In FIG. 8 and FIG. 9, when mixed-type images are captured, each set of mixed-type images always consists of one special image and one regular image.

Figure 10:
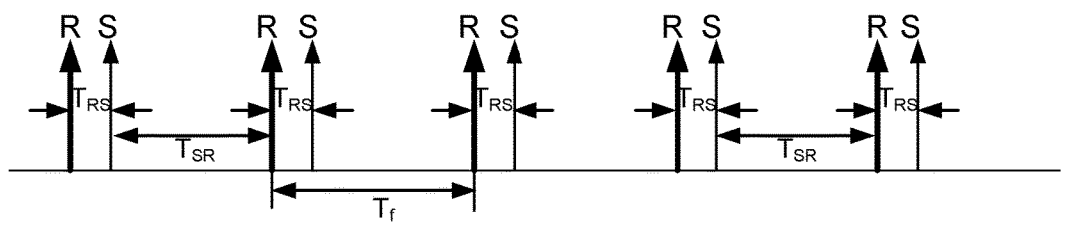
FIG. 10 illustrates an embodiment of the present invention, where SLI is captured after each associated regular image as shown.
Figure 11:
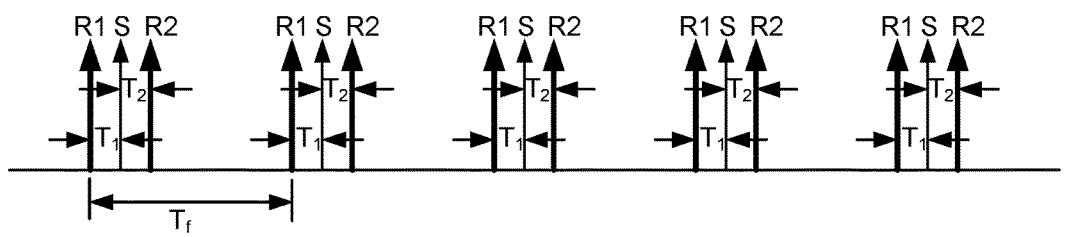

In U.S. patent application Ser. No. 14/884,788, filed on Oct. 16, 2015, a capsule camera system for capturing mixed structured-light images (SLIs) and regular images is disclosed, where the SLIs are captured by setting the sensor to a lower dynamic range. In U.S. patent application Ser. No. 14/884,788, an SLI can be captured prior to or after the associated regular image. In U.S. patent application Ser. No. 15/333,071, filed on Oct. 24, 2016, a method to capture an SLI between two regular sub-images is disclosed, where two regular sub-images are combined into one regular image. Since the SLI image is captured at the time instance between the two regular sub-images, the depth information derived from the SLI should correlate more closely with the combined regular image. The method of configuring the capsule camera mentioned above can be applied to this case to cause the energy-based frame times of the special image (i.e., the SLI) and the associated regular image closer than the average frame time. Furthermore, in one embodiment, the time distance between the energy-based frame times of the special image (i.e., the SLI) and the associated regular image can be substantially reduced, such as to be less than half of the average frame period. An embodiment of the present invention can capture an SLI prior to the associated regular image as shown FIG. 8, which is similar to the case that a regular image is always captured after a monitor-mode image. In another example, the SLI is captured after each associated regular image as shown in FIG. 10. Another embodiment of the present invention is shown in FIG. 11, where two regular sub-images are captured with an SLI captured in between. The capsule camera is configured to cause the time distance between the energy-based frame times of the special image (i.e., the SLI) and the associated regular sub-images substantially reduced. The time distance between the energy-based frame times of the special image and the associated first regular sub-image (i.e., R1) is designated as $T_1$ and the time distance between the energy-based frame times of the special image and the associated second regular sub-image (i.e., R2) is designated as $T_2$. In this case, each set of mixed-type images consists of one SLI (i.e., S) and two regular sub-images (i.e., R1 and R2). The two regular sub-images are counted as one regular image for calculating the average frame period. Since there are two regular sub-images, the time distance between the energy-based frame times of the special image and the associated combined regular image is calculated as the average of $T_1$ and $T_2$. According to one embodiment, $T_1$ is equal to $T_2$ if the absorbed light energy for R1 and R2 are the same. However, $T_1$ can also be different from $T_2$.

Figure 12:
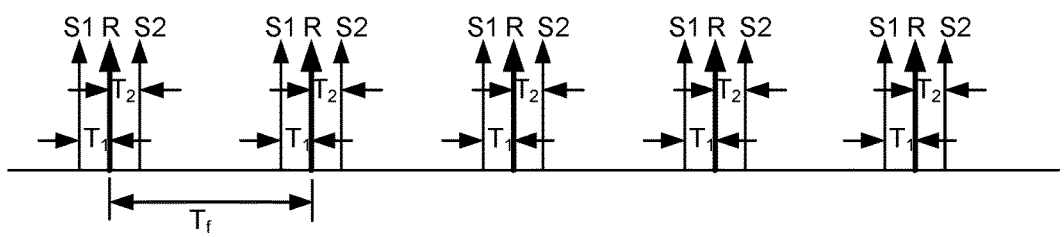

The energy-based frame times for special images and regular images as illustrated in FIG. 8, FIG. 10 and FIG. 11 may also be applied to multi-spectral imaging. In this case, the regular image may correspond to a wide-band image and the special image may correspond to a narrow band image. Since multiple narrow band images may be used for an associated wide-band image, a set of mixed-type image for the multiple spectral imaging may consist of one regular image and two or more special images. FIG. 12 illustrates an example of one regular image with two special images for narrow-band imaging, where the regular image corresponds to a wideband image and the special images S1 and S2 correspond to two different narrow-band images.

In another embodiment, the delay period after an image is captured can be further reduced by increasing the clock of the processor (e.g. CPU, microcontroller, DSP (Digital Signal Processor) or FPGA (Field Programmable Gate Array) that is programmed to make various decisions or calculations, such as the activity derivation and mode decision, or the clock to sensor to speed up sensor operation. By increasing the clock speed, the command execution speed can be increased accordingly. Therefore, the mode decision, particularly for the Monitor mode, can be made sooner so that the next frame start for a Capture mode can be triggered sooner.

Figure 13:
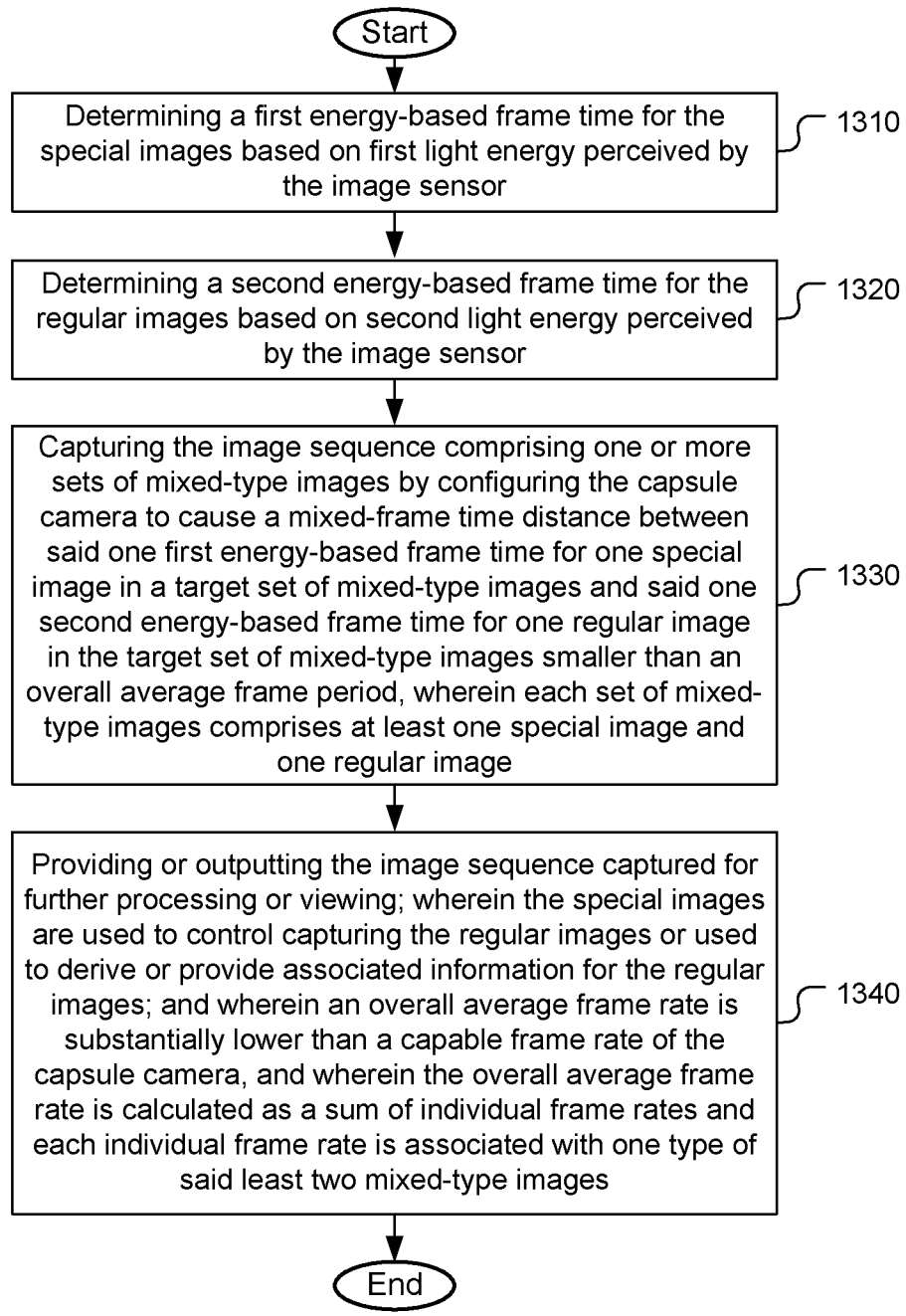
FIG. 13 illustrates an exemplary flowchart for a system incorporating an embodiment of the present invention to cause mixed-frame distance between the first energy-based frame time for one special image in a target set of mixed-type images and the second energy-based frame time for one regular image in the target set of mixed-type images smaller than an average frame period.

FIG. 13 illustrates an exemplary flowchart for a system incorporating an embodiment of the present invention to cause mixed-frame distance between the first energy-based frame time for one special image in a target set of mixed-type images and the second energy-based frame time for one regular image in the target set of mixed-type images smaller than an average frame period. The flowchart may correspond to software program codes to be executed on a computer, a server, a digital signal processor or a programmable device or embedded system for the case of an autonomous capsule for the disclosed invention. The program codes may be written in various programming languages. The flowchart may also correspond to hardware based implementation, where one or more electronic circuits (e.g. ASIC (application specific integrated circuits) and FPGA (field programmable gate array)) or processors (e.g. DSP (digital signal processor and memories)) are used. According to this method, a first energy-based frame time for the special images is determined based on first light energy perceived by the image sensor in step 1310 and a second energy-based frame time for the regular images is determined based on second light energy perceived by the image sensor. The image sequence comprising one or more sets of mixed-type images is captured by configuring the capsule camera to cause a mixed-frame distance between the first energy-based frame time for one special image in a target set of mixed-type images and the second energy-based frame time for one regular image in the target set of mixed-type images smaller than an average frame period in step 1330, where each set of mixed-type images comprises at least one special image and one regular image. The energy perceived by sensor can be determined by the light source driver in the capsule system. The image sequence captured is then outputted in step 1340. The special images are used to control capturing the regular images or used to derive or provide associated information for the regular images. The image sequence is captured at a frame rate substantially lower than a capable frame rate of the capsule camera.

The invention may be embodied in other specific forms without departing from its spirit or essential characteristics. The described examples are to be considered in all respects only as illustrative and not restrictive. Therefore, the scope of the invention is indicated by the appended claims rather than by the foregoing description. All changes which come within the meaning and range of equivalency of the claims are to be embraced within their scope.

The invention claimed is:

1. A method of capturing an image sequence using a capsule camera when the capsule camera travels through a human gastrointestinal tract after the capsule camera is swallowed by a patient, wherein the capsule camera comprises an image sensor and is capable of capturing at least two mixed-type images corresponding to special images and regular images, the method comprising:

determining one first energy-based frame time for the special images based on first light energy perceived by the image sensor;

determining one second energy-based frame time for the regular images based on second light energy perceived by the image sensor;

capturing the image sequence comprising one or more sets of mixed-type images by configuring the capsule camera to cause a mixed-frame time distance between said one first energy-based frame time for one special image in a target set of mixed-type images and said one second energy-based frame time for one regular image in the target set of mixed-type images smaller than an overall average frame period, wherein each set of mixed-type images comprises at least one special image and one regular image; and providing or outputting the image sequence captured for further processing or viewing; and wherein the special images are used to control capturing the regular images or used to derive or provide associated information for the regular images; and wherein an overall average frame rate is substantially lower than a capable frame rate of the capsule camera, and wherein the overall average frame rate is calculated as a sum of individual frame rates and each individual frame rate is associated with one type of said least two mixed-type images.

2. The method of claim 1, wherein the first light energy perceived by the image sensor is determined by accumulating first illumination power from a light source over a first integration period of the image sensor for the special images and the second light energy perceived by the image sensor is determined by accumulating second illumination power from the light source over a second integration period of the image sensor for the regular images.

3. The method of claim 1, wherein said one first energy-based frame time is determined at a first time instance when the first light energy exceeds a first energy threshold for a target special image and said one second energy-based frame time is determined at a second time instance when the second light energy exceeds a second energy threshold for a target regular image.

4. The method of claim 3, wherein the first energy threshold is set to a half of total accumulated first light energy over a first integration period of the image sensor and the second energy threshold is set to a half of total accumulated second light energy over a second integration period of the image sensor.

5. The method of claim 1, wherein the mixed-frame time distance is smaller than 90 percent of an overall average frame period corresponding to an inverse of the overall average frame rate.

6. The method of claim 1, wherein the special images are captured with a lower quality.

7. The method of claim 6, wherein the lower quality corresponds to lower image dynamic range, lower spatial resolution, smaller image size, or a combination thereof.

8. The method of claim 1, wherein the special images correspond to structured-light images (SLIs) used to derive depth information for associated regular images.

9. The method of claim 8, wherein each set of mixed-type images consists of one structured-light image (SLI) and one regular image.

10. The method of claim 9, wherein said one structured-light image (SLI) is captured prior to said one regular image.

11. The method of claim 9, wherein said one structured-light image (SLI) is captured after said one regular image.

12. The method of claim 8, wherein each set of mixed-type images consists of one structured-light image (SLI) and two regular sub-images, and wherein the structured-light image is captured between the two regular sub-images and the mixed-frame time distance is derived based on two mixed-frame time distances associated with the structured-light image and the two regular sub-images respectively.

13. The method of claim 12, wherein the two regular sub-images are combined to form one regular image.

14. The method of claim 1, wherein the special images correspond to monitor-mode images used to control capturing the regular images.

15. The method of claim 14, wherein each set of mixed-type images consists of one monitor-mode image and one or more regular images.

16. The method of claim 14, wherein an activity metric is determined between one monitor-mode image and one previously captured image, and when the activity metric exceeds a threshold, one or more regular images are captured to form one set of mixed-types of images along with said one monitor-mode image.

17. The method of claim 16, wherein when the activity metric does not exceed the threshold, a next monitor-mode image is captured.

18. The method of claim 1, wherein the special images correspond to narrow-band images and the regular images correspond to wide-band images.

19. The method of claim 18, wherein each set of mixed-type images consists of one wide-band image and narrow-band images.

20. An apparatus for capturing an image sequence using a capsule camera when the capsule camera travels through a human gastrointestinal tract after the capsule camera is swallowed by a patient, wherein the capsule camera comprises an image sensor and is capable of capturing at least two mixed-type images corresponding to special images and regular images, the apparatus comprising one or more electronic circuits or processors arranged to:

determining one first energy-based frame time for the special images based on first light energy perceived by the image sensor;

determine one second energy-based frame time for the regular images based on second light energy perceived by the image sensor;

capture the image sequence comprising one or more sets of mixed-type images by configuring the capsule camera to cause a mixed-frame time distance between said one first energy-based frame time for one special image in a target set of mixed-type images and said one second energy-based frame time for one regular image in the target set of mixed-type images smaller than an overall average frame period, wherein each set of mixed-type images comprises at least one special image and one regular image; and provide or output the image sequence captured for further processing or viewing; and wherein the special images are used to control capturing the regular images or used to derive or provide associated information for the regular images; and wherein an overall average frame rate is substantially lower than a capable frame rate of the capsule camera, and wherein the overall average frame rate is calculated as a sum of individual frame rates and each individual frame rate is associated with one type of said least two mixed-type images.

* * * * *